United States Patent
Jung

(10) Patent No.: US 10,572,999 B2
(45) Date of Patent: Feb. 25, 2020

(54) VASCULAR TERRITORY SEGMENTATION USING MUTUAL CLUSTERING INFORMATION FROM IMAGE SPACE AND LABEL SPACE

(71) Applicant: Wake Forest University Health Sciences, Winston-Salem, NC (US)

(72) Inventor: Youngkyoo Jung, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 179 days.

(21) Appl. No.: 15/843,708

(22) Filed: Dec. 15, 2017

(65) Prior Publication Data

US 2018/0225821 A1    Aug. 9, 2018

Related U.S. Application Data

(63) Continuation of application No. 14/775,271, filed as application No. PCT/US2014/020552 on Mar. 5, 2014, now Pat. No. 9,865,051.

(Continued)

(51) Int. Cl.
*G06T 7/00*    (2017.01)
*G06T 7/155*   (2017.01)
(Continued)

(52) U.S. Cl.
CPC .......... *G06T 7/0012* (2013.01); *A61B 5/0042* (2013.01); *A61B 5/026* (2013.01); *A61B 5/0263* (2013.01); *A61B 5/743* (2013.01); *A61B 5/7445* (2013.01); *G06T 7/155* (2017.01); *G06T 7/90* (2017.01); *G06T 11/008* (2013.01);
(Continued)

(58) Field of Classification Search
CPC .............................. G06T 7/0012; A61B 5/026
See application file for complete search history.

(56) References Cited

U.S. PATENT DOCUMENTS 6,792,302 B2    9/2004  Wintermark et al.
7,069,068 B1 *  6/2006  Ostergaard ............ A61B 5/055
                                                324/307

(Continued)

FOREIGN PATENT DOCUMENTS

EP        1 886 254      2/2008
WO    WO 2006/127687    11/2006

(Continued)

OTHER PUBLICATIONS

Aibinu et al., MRI Reconstruction Using Discrete Fourier Transform: A tutorial, World Academy of Science, Engineering and Technology, 2008, pp. 179-185, vol. 42.

(Continued)

*Primary Examiner* — Nay A Maung
*Assistant Examiner* — Jose Torres
(74) *Attorney, Agent, or Firm* — Myers Bigel, P.A.

(57) ABSTRACT

Methods, systems, computer programs, circuits and workstations are configured to generate at least one two-dimensional weighted CBF territory map of color-coded source artery locations using an automated vascular segmentation process to identify source locations using mutual connectivity in both image and label space.

15 Claims, 7 Drawing Sheets
(4 of 7 Drawing Sheet(s) Filed in Color)

Related U.S. Application Data

(60) Provisional application No. 61/788,826, filed on Mar. 15, 2013.

(51) Int. Cl.
 *G06T 7/90* (2017.01)
 *A61B 5/026* (2006.01)
 *A61B 5/00* (2006.01)
 *G06T 11/00* (2006.01)

(52) U.S. Cl.
 CPC ............ *G06T 2207/10081* (2013.01); *G06T 2207/10088* (2013.01); *G06T 2207/30016* (2013.01); *G06T 2207/30101* (2013.01)

(56) References Cited

U.S. PATENT DOCUMENTS

| | | | |
|---|---|---|---|
| 7,545,142 | B2 | 6/2009 | Alsop |
| 7,587,233 | B2 | 9/2009 | Wong et al. |
| 7,627,360 | B2 | 12/2009 | Kimura |
| 7,898,254 | B2 | 3/2011 | Feinberg et al. |
| 2008/0269595 | A1 | 10/2008 | Wong |
| 2009/0149733 | A1 | 6/2009 | Guenther |
| 2010/0240983 | A1 | 9/2010 | June et al. |
| 2010/0274117 | A1 | 10/2010 | Gunther et al. |
| 2011/0170759 | A1 | 7/2011 | Bjornerud et al. |
| 2012/0243761 | A1 | 9/2012 | Senzig et al. |
| 2012/0271157 | A1 | 10/2012 | Wong et al. |
| 2013/0231554 | A1 | 9/2013 | Jung |
| 2013/0253895 | A1* | 9/2013 | Okell ............... A61B 6/507 703/11 |
| 2014/0270442 | A1 | 9/2014 | Jung |

FOREIGN PATENT DOCUMENTS

| | | |
|---|---|---|
| WO | WO 2010/108161 | 9/2010 |
| WO | WO 2011/130581 | 10/2011 |

OTHER PUBLICATIONS

Alsop "ASL Perfusion Imaging: Concepts and Applications", *International Society for Magnetic Resonance in Medicine*, May 6, 2006, 5 Pages.

Chappell et al. "A General Framework for the Analysis of Vessel Encoded Arterial Spin Labeling for Vascular Territory Mapping", *Magnetic Resonance in Medicine*, 64:1529-1539, 2010.

Dai et al. "Modified pulsed continuous arterial spin labeling for labeling of a single artery", *Magnetic Resonance in Medicine*, vol. 64, No. 4, Jul. 27, 2010, pp. 975-982.

Essig et a., The Five Most Frequently Asked Technical Questions, AJR Am J Roentgenol., Jan. 2013, 200:1.

Feinberg et al. "Halving MR Imaging Time by Conjugation: Demonstration at 3.5 kG$^1$", *Radiology*, 1986; 161:527-531.

Gevers et al. "Robustness and Reproducibility of Flow Territories Defined by Planning-Free Vessel-Encoded Pseudocontinuous Arterial Spin-Labeling", *AJNR American Journal of Neuroradiology*, 33:E21-E25, Feb. 2012, Mar. 10, 2011 (Epub Ahead of Print).

Hartkamp et al. "Mapping of cerebral perfusion territories using territorial arterial spin labeling: techniques and clinical application" NMR Biomed. DOI:10.1002/nbm.2836, Jul. 15, 2012.

Hayasaka et al. "Combining voxel intensity and cluster extent with permutation test framework" Neurolmage 23 (2004) 54-63.

International Search Report corresponding PCT Application No. PCT/US2014/020552, 4 pages, dated Jul. 7, 2014.

International Search Report and Written Opinion for related PCT Application No. PCT/US2013/028919, 12 pages, dated Jun. 14, 2013.

Jung "Vessel Encoded Arterial Spin Labeling Using Fourier Encoding", *Proceedings of the International Society for Magnetic Resonance in Medicine*, Melbourne, Australia, May 5-11, 2012, p. 581.

Jung et al. "Probabilistic Cerebral Vascular Territory Atlases", *Proceedings of the 22$^{nd}$ Annual Meeting of ISMRM*, Milan, Italy, May 2014, p. 422.

Jung et al. "Vascular Territory Segmentation Using Mutual Clustering in Image and Label Space", ISMRM:581, Apr. 2013.

Jung et al., Multiphase Pseudocontinuous Arterial Spin Labeling (MP-PCASL) for Robust Quantification of Cerebral Blood Flow, Magnetic Resonance in Medicine, 2010, pp. 799-810, vol. 64.

Kansagra et al. "Quantitative Assessment of Mixed Cerebral Vascular Territory Supply With Vessel Encoded Arterial Spin Labeling MRI", *Stroke*, Aug. 14, 2008, 39:2980-2985.

Kansagra et al., Improved estimation of cerebral artery branch territories using cluster-based segmentation of vessel-encoded pseudocontinuous ASL data, Proc. Intl. Soc. Mag. Reson. Med, 2012, pp. 583, vol. 20.

Kansagra et al., Mapping of Vertebral Artery Perfusion Territories Using Arterial Spin Labeling MRI, Journal of Magnetic Resonance Imaging , 2008, pp. 762-766, vol. 28.

Mohajar, Cluster analysis of the signal curves in perfusion DCE-MRI datasets, Munche, Jul. 2, 2012, thesis paper, 190 pages.

Moratal et al., k-Space tutorial: an MRI educational tool for a better understanding of k-space, Biomedical Imaging and Intervention Journal, 2008, 8 pages, vol. 4, No. 1, e15.

Seidenwurm et al. "Performance Measures in Neuroradiology", *AJNR American Journal of Neuroradiology*, 28:1435-1438, Sep. 2007.

Tholen et al. "Suspected Carotid Artery Stenosis: Cost-effectiveness of CT Angiography in Work-up of Patients with Recent TIA or Minor Ischemic Stroke", *Radiology*, vol. 256, No. 2, Aug. 2010, pp. 585-597.

Wardlaw et al. "Non-invasive imaging compared with intra-arterial angiography in the diagnosis of symptomatic carotid stenosis: a meta-analysis", *The Lancet*, vol. 367, Issue 9521, May 6-12, 2006, pp. 1503-1512.

Wong "Vessel-Encoded Arterial Spin-Labeling Using Pseudocontinuous Tagging" MRM, 58:1086-1091, 2007.

Wong et al. "Blind Detection of Source Vessel Locations and Resonance Offsets using Randomly Encoded VEASL" 19$^{th}$ ISMRM: 294, 2011.

Wong et al. "Blind detection of vascular sources and territories using random vessel encoded arterial spin labeling", *Magnetic Resonance Materials in Physics Biology and Medicine*, 25(2):95-101, Received: Aug. 14, 2011, Published Online: Jan. 10, 2012, 7 Pages.

Wu et al., Collateral Circulation Imaging: MR Perfusion Territory Arterial Spin-Labeling at 3T, Am J Neuroradiol, 2008, pp. 1855-1860, vol. 29.

* cited by examiner

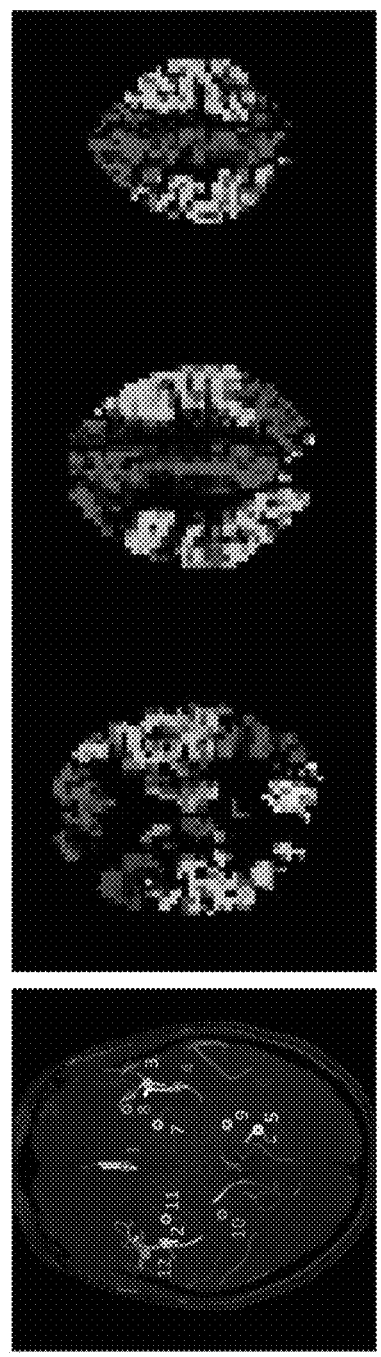
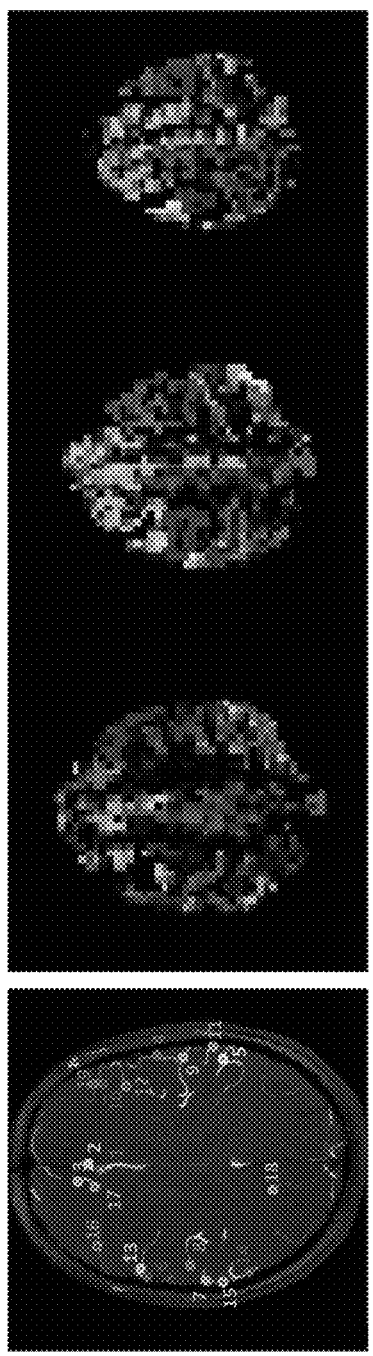
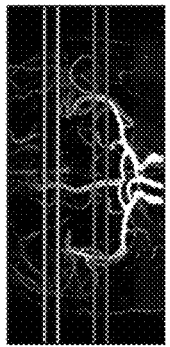
FIG. 2A
FIG. 2B
FIG. 2C
FIG. 2D
FIG. 2E

VASCULAR TERRITORY SEGMENTATION USING MUTUAL CLUSTERING INFORMATION FROM IMAGE SPACE AND LABEL SPACE

RELATED APPLICATIONS

This application is a continuation of U.S. application Ser. No. 14/775,271, filed Sep. 11, 2015, which is a § 371 national phase application of PCT/US2014/020552, filed Mar. 5, 2014, which claims the benefit of and priority to U.S. Provisional Application Ser. No. 61/788,826, filed Mar. 15, 2013, the contents of which are hereby incorporated by reference as if recited in full herein.

BACKGROUND

Carotid or vertebrobasilar stenosis restricts distal blood flow, which decreases blood supply to the parts of the brain subserved by these vessels, and increases the risk of ischemic stroke. Surgical intervention with carotid endarterectomy or endovascular angioplasty/stenting is generally pursued if the diameter of the lumen of the internal carotid artery (ICA) is reduced more than 70%, which is typically documented by noninvasive imaging. Collateral circulation increases in the brain as a normal physiologic mechanism to by-pass and compensate for the blockage in the main artery. In some cases, this increased collateral flow can supply enough oxygenated blood to maintain adequate cerebral perfusion for supporting brain function in symptom free patients. The importance of adequate hemodynamic compensation via collateral circulation has been shown in patients with cerebral arterial stenosis.

Focal arterial stenosis can be clinically evaluated using a variety of imaging methods, including duplex ultrasound, computed tomography angiogram (CTA), and magnetic resonance angiography (MRA). Although invasive CT-based methods have been used for qualitative assessment of vascular territory perfusion, quantitative mapping of blood flow from individual source arteries is still not practical in the clinical setting. Vascular territory mapping using arterial spin labeling (ASL) has been proposed, but currently typically requires complicated planning prior to scanning and extensive post-processing, which hinders the practical clinical use of these methods. Psuedo-continuous ASL (PCASL) tagging can be used for vessel-encoded ASL (VE-ASL) utilizing gradients applied during the tagging period to spatially encode multiple feeding arteries. See, e.g., Wong, MRM, 58: 1086-1091, 2007; ISMRIM; 581, 2012; and Wong and Guo, MAGMA 25: 95-101, 2012. Strategies has been devised for the detection of source arteries without a priori knowledge of vessel locations using a random encoding scheme (see, Wong & Guo, 19th ISMRM: 294, 2011) or a Fourier encoding scheme (see, Jung, 20th ISMRM: 581, 2012). The source artery location at the labeling plane is estimated on a voxel-wise basis in the image volume but a territory often needs to be manually identified. The source location of a territory is often widespread due to noise and large vessel diameters, becoming more complicated when the labeling plane includes a large number of source arteries.

There is a need for clinically acceptable methods for visualization and quantification of perfusion territories from major feeding arteries in the brain.

SUMMARY OF EMBODIMENTS OF THE INVENTION

Embodiments of the invention are directed to methods, systems and circuits that can automatically segment an image volume into separate vascular territories using mutual clustering in image and label space.

Embodiments of the invention provide systems, methods, circuits, workstations and methods suitable for automated vascular territory mapping for resolving source locations and to determine if multiple sources in different perfusion territories are from a single artery.

Embodiments of the invention may be particularly useful for MRI brain scans for evaluation of large artery diseases, cerebral vascular disease, and carotid stenosis and may also be useful for stroke, especially thromboembolic stroke, and/or for evaluation of treatments or clinical trials.

Embodiments of the invention may be implemented as a routine brain scan for neurological evaluations due to the automated processing and short MRI signal acquisition time required for vascular mapping that can be provided in a color map that represents both location of source arteries (typically by a predefined different color for each artery and/or location direction) and amount of perfusion (typically in brightness and/or opacity).

Some embodiments are directed to methods of color mapping brain vascular perfusion using MRI. The color map can indicate the associated feeding artery per voxel in unique colors. For example, right internal carotid artery may be depicted in blue, left internal carotid artery in red, and right vertebral artery in cyan, and left vertebral artery in yellow.

The methods can include displaying the at least one map on a clinician workstation.

The segmentation analysis can be carried out using a processor associated with an MR Scanner and/or at least one clinician workstation.

Some embodiments are directed to image and/or data processing circuits configured to carry out any of the above steps or features.

It is noted that aspects of the invention described with respect to one embodiment, may be incorporated in a different embodiment although not specifically described relative thereto. That is, all embodiments and/or features of any embodiment can be combined in any way and/or combination. Further, any feature or sub-feature claimed with respect to one claim may be included in another future claim without reservation and such shall be deemed supported in the claims as filed. Thus, for example, any feature claimed with respect to a method claim can be alternatively claimed as part of a system, circuit, computer readable program code or workstation. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A is an image with exemplary label plane locations according to embodiments of the present invention.

FIG. 2B shows the estimated source locations overlaid on maximum intensity projection (MIP) of the upper label location of FIG. 2A.

FIG. 2C shows corresponding CBF weighted territory maps for FIG. 2B.

FIG. 2D is an image with estimated source locations overlaid on MIP of the lower label location of FIG. 2A.

FIG. 2E shows corresponding CBF weighted territory maps for FIG. 2D.

DETAILED DESCRIPTION

Figure 1:
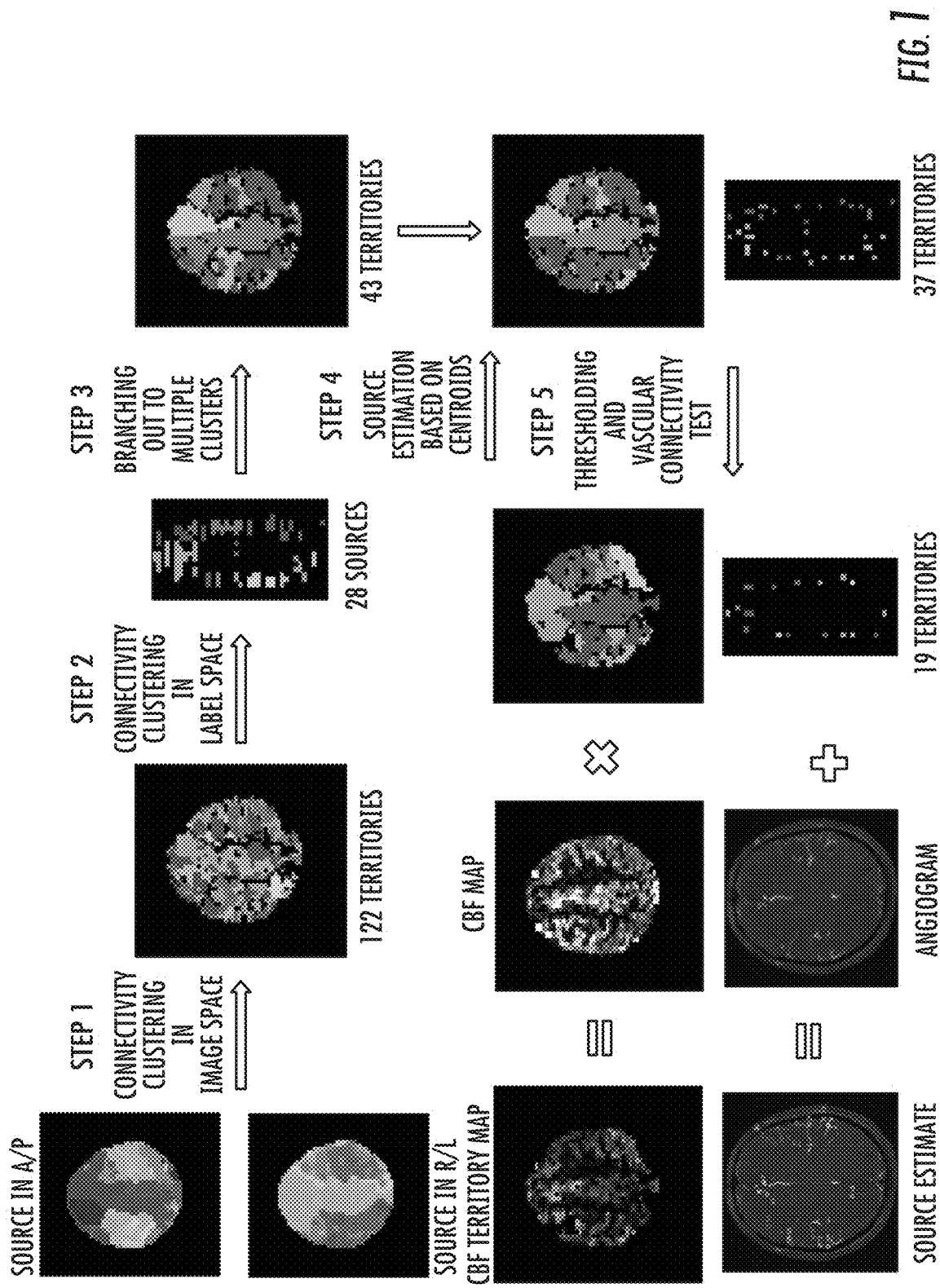
FIG. 1 is a schematic illustration of a sequence of exemplary automated vascular segmentation steps for vascular territory mapping according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various actions, steps or components and should not be limited by these terms. These terms are only used to distinguish one action, step or component from another action, step or component. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "circuit" refers to an entirely software embodiment or an embodiment combining software and hardware aspects, features and/or components (including, for example, a processor and software associated therewith embedded therein and/or executable by, for programmatically directing and/or performing certain described actions or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MRI scanner" or MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5T/3.0T; Philips Medical Systems: Achieva 1.5T/3.0T; Integra 1.5T; Siemens: MAGNETOM Avanto; MAGNETOM Espree; MAGNETOM Symphony; MAGNETOM Trio; MAGNETOM Verio; and SKYRA scanner. As is well known, the MR scanner can include a main operating/control system that is housed in one or more cabinets that reside in an MR control room while the MRI magnet resides in the MR scan room. The control room and scan room can be referred to as an MR suite and the two rooms can be separated by an RF shield wall. The term "high-magnetic field" refers to field strengths above about 0.5 T, typically above 1.0 T, and more typically between about 1.5 T and 10 T. Embodiments of the invention may be particularly suitable for 1.5 T, 2.0 T and 3.0 T systems, or higher field systems such as future contemplated systems at 4.0 T, 5.0 T, 6.0 T and the like. The methods and systems can also be applied to animal MRI data acquired from animal MRI scanners. The term "patient" refers to humans and animals.

The term "automatically" and derivatives thereof means that the operation and/or method can be substantially, and typically entirely, carried out without manual input, and is typically programmatically directed and/or carried out. The term "electronically" with respect to connections includes both wireless and wired connections between components.

The term "clinician" means physician, neurologist, radiologist, physicist, or other medical personnel desiring to review medical data of a patient. The term "workstation" refers to a display and/or computer associated with a clinician.

The term "reconstruction" is used broadly to refer to original or post-acquisition and storage and subsequent construction of image slices or images of an image data set.

Each article, reference and patent cited or discussed herein is hereby incorporated by reference as if recited in full herein.

Embodiments of the invention are particularly suitable for evaluating MRI image data but can also be useful for post-acquisition analysis of image data from other imaging modalities, including CT (computed tomography) and PET (Positron Emission Tomography), for example.

The term "color-coded" (or color-encoded) refer to a defined unique color or color scale of pixels/voxels correlated to source artery location and/or blood flow direction to illustrate vessel (e.g., source artery) and blood flow direction.

The color map(s) can have both x- and y-directional modulation so that a user can visually ascertain which source artery and/or direction the source artery is located for particular perfusion regions. The color map(s) can indicate the associated feeding artery per voxel in unique colors. For example, right internal carotid artery may be displayed in blue, left internal carotid artery in red, and right vertebral artery in cyan, and left vertebral artery in yellow. Thus, for example, in x-direction modulation, a first color, such as blue, represents that the source artery is to the right while a second color, such as red, indicates that the source artery is to the left. One color, e.g., red, can refer to "from anterior" and another color, e.g., yellow, can refer to "from posterior" in y directional modulation. The color-coded map can also be configured to illustrate an amount of perfusion by a scale of brightness such that brightness indicates intensity of each voxel that is proportional to blood flow for a respective voxel. Also, to comply with patent filing rules, black and white copies or grey scale versions of these images may be used in support of the application.

The term "about" refers to a parameter that can vary from the recited value, typically between +/−20%. For time parameters in minutes or hours, for example, the stated value includes times that are +/−5 minutes of that number.

The term "time of flight" (TOF) refers to MRI angiography that is based on the phenomenon of flow-related enhancement of spins entering into an imaging slice. As a result of being unsaturated, these spins can produce more signal that surrounding stationary spins.

PCASL-based VE-ASL methods often require long scan times and complicated clustering algorithms to classify multiple vascular territories. Embodiments of the invention can be used as an analysis tool or module with systems that are configured to perform VE-ASL.

The term "label space" refers to the 2-D space in the neck of a patient where blood signal is labeled when it passes a respective defined plane.

The term "cluster" or "clustering" refers to a set of contiguous or neighboring voxels of image data that have at least one substantially similar (e.g., the same) value image parameter. Typically, the image parameter is source location in Cartesian coordinates (e.g., a cluster of neighboring voxels having an intensity at the same x, y position or within 1 unit of position in either an x- or y- or x- and y-direction). For example, voxels sharing at least one common edge can be considered as neighbors (the 18 connectivity scheme for a 3-D image). For example, for a 3×3×3 voxel cube in a 3-D space, all the voxels including or except eight corner voxels are considered to be connected to the voxel at the center.

The term "territory" and derivatives thereof refer to renderings of (2-D or 3-D) vascular maps with related vascular sources or related potential vascular sources identified in like color. The term "clustered territory" means a 2-D or 3-D territory that has at least one common x, y source vessel location based on electronically identified clusters of like voxels.

The terms "weighted CBF territory map" and "CBF weighted territory map" are used interchangeably and mean that proportions of blood flow indicated in the map are scaled to reflect qualitative or quantitative measures of blood flow, preferably quantitative measures of blood flow.

Generally stated, embodiments of the invention provide automated vascular territory segmentation algorithms using connectivity information from both image space and label space. The territory segmentation algorithms have two assumptions: (1) a territory may have multiple source locations depending on the detection resolution, vessel diameter, and vessel turns in the label plane but the multiple locations must be neighboring; and (2) a single artery may supply multiple non-contiguous areas because of branching after leaving the labeling plane.

FIG. 1 illustrates an example of a sequence of analysis steps that can be used to provide an automated (electronic) vascular territory segmentation to segment an image volume into separate vascular territories. FIG. 1 illustrates steps of a segmentation algorithm or module that uses source location in (x, y) coordinates of a coordinate system. The coordinate system is typically a Cartesian coordinate system.

First (shown as Step 1), three dimensional (3-D) connectivity can be applied to source image data to identify clustering with a small cluster size in image space on a voxel-wise basis to generate clustered territories. Each clustered territory has a same source location in (x, y) coordinates. The clustering can identify small clusters of contiguous or neighboring voxels of at least about 4-6 voxels that have the same source location. The small cluster size can include clusters of at least 4-6 neighboring voxels, typically 4 or more neighboring voxels. Smaller clusters, with a smaller cluster size less than 4 neighboring voxels, can be used as a threshold to reject associated voxels as being contaminated by noise. The 3-D connectivity can be carried out simply using physical contiguity. For example, the voxels having connectivity are voxels that are physically in contact in the image space. The source image data can include any medical image data set. In some embodiments, the source image data comprises MRI image data of a patient's brain with source locations in A/P and R/L directions.

Next (shown as Step 2 in FIG. 1), the source locations of territories from Step 1 are mapped in 2-D label space and the sources are clustered based on spatial connectivity. The 2-D clustering can be carried out again based simply on physical contiguity and/or based on a statistical distribution. In particular embodiments, the 2-D clustering analysis that establishes source locations is based on physical contact. This is applied based on assumption 1 noted above.

As shown in Step 3, territories corresponding to the source clusters from Step 2 are generated. Multiple 3-D spatial clusters may stem from a single source based on assumption 2.

Next, as shown in Step 4, from each territory identified in Step 3, the center of mass (e.g., the centroid) to label space is calculated and tested to determine if multiple territories are from a same source. Clusters are regarded from the same source if the calculated distances between cluster centroids is smaller than a detection resolution defined in the source image data. For example, the case shown in FIG. 1 has the detection resolutions of 3 mm in A/P (or in y-direction) and 9 mm in R/L (or in x-direction). The clustered source(s) in Step 2 may now be separated into multiple sources if the distances between cluster centroids are larger than the detection resolution. The separation may indicate that the multiple sources were clustered in Step 2 due to proximity but they act as independent sources. As shown for Step 5, a thresholding and vascular connectivity test can be carried out for further resolving source location using the centroid calculations and sources can be numbered and presented in color coding. The analysis can identify a reduced number of territories relative to the thresholding and vascular connectivity test. Small territories (e.g., about 30 voxels or less) can be rejected as not containing sufficient vascular source information and hence are not used to create a CBF territory map.

Optionally, source locations of surviving territories can be validated at this stage using a high resolution MR angiogram with a region growing algorithm obtained at the label plane to determine if multiple sources are from the same artery. The "validation" may be particularly appropriate where a single artery generates two source locations in a territory due to a lateral turn in labeling space.

As shown in FIG. 1, the CBF map and MRA (if provided) can be used to generate a CBF color territory map and a separate source estimation map with sources identified in color and number. The source estimation map numbers can be ordered based on cluster size, from smallest to largest (or the reverse).

The above analysis protocol/algorithm was tested using data obtained with Fourier encoded ASL (2) in the A/P direction and with a phase offset in the R/L direction. The detection resolution was 3 mm in A/P and 9 mm in R/L. A maximum intensity projection (MIP) image from a time-of-flight angiogram (1 cm thickness) was used to overlay estimates of source locations and determine if multiple sources are from a single artery moving laterally within the labeling space.

FIGS. 2A-2E show results from placement of the labeling plane at two locations: a superior location where multiple branches of the middle cerebral artery supply cortical gyri (blue in FIG. 2A), and a more inferior location 2 cm above the circle of Willis (red in FIG. 2B). The proposed algorithm segmented the images into 19 (FIG. 2B) and 12 perfusion territories (FIG. 2C), respectively. There was one territory in which two sources were actually from a single artery due to lateral turn in the labeling space. Small branches from thalamo-perforators to the thalamus (orange and blue, source 9 and 10, FIG. 2C) and lenticulostriates to the basal ganglia (green, sources 11 and 7, FIG. 2C) are identified. The algorithm was able to resolve separate territories even with the neighboring sources (purple and blue, sources 10 and 19, FIG. 2B).

FIG. 2A shows the label plane locations "upper" and "lower." FIGS. 2B and 2-D show the estimated source locations overlaid on MIP images of the respective label location and FIGS. 2C and 2E show corresponding CBF weighted territory maps from the upper (FIG. 2C) and the lower (FIG. 2-D) labeling locations. Numbering was ordered based on cluster size.

Because the analysis method/circuit or program uses mutual connectivity in both image and label space, the capability of segmenting two neighboring territories can be limited when they are clustered in Step 2 and 3. As noted above, a high detection resolution may be used to confirm a separation in this situation. Verification of the vascular connectivity in Step 5 may also or alternatively use manual editing. However, the analysis may potentially be totally automated through the use of a high resolution MRA and a region growing algorithm.

Figure 3:
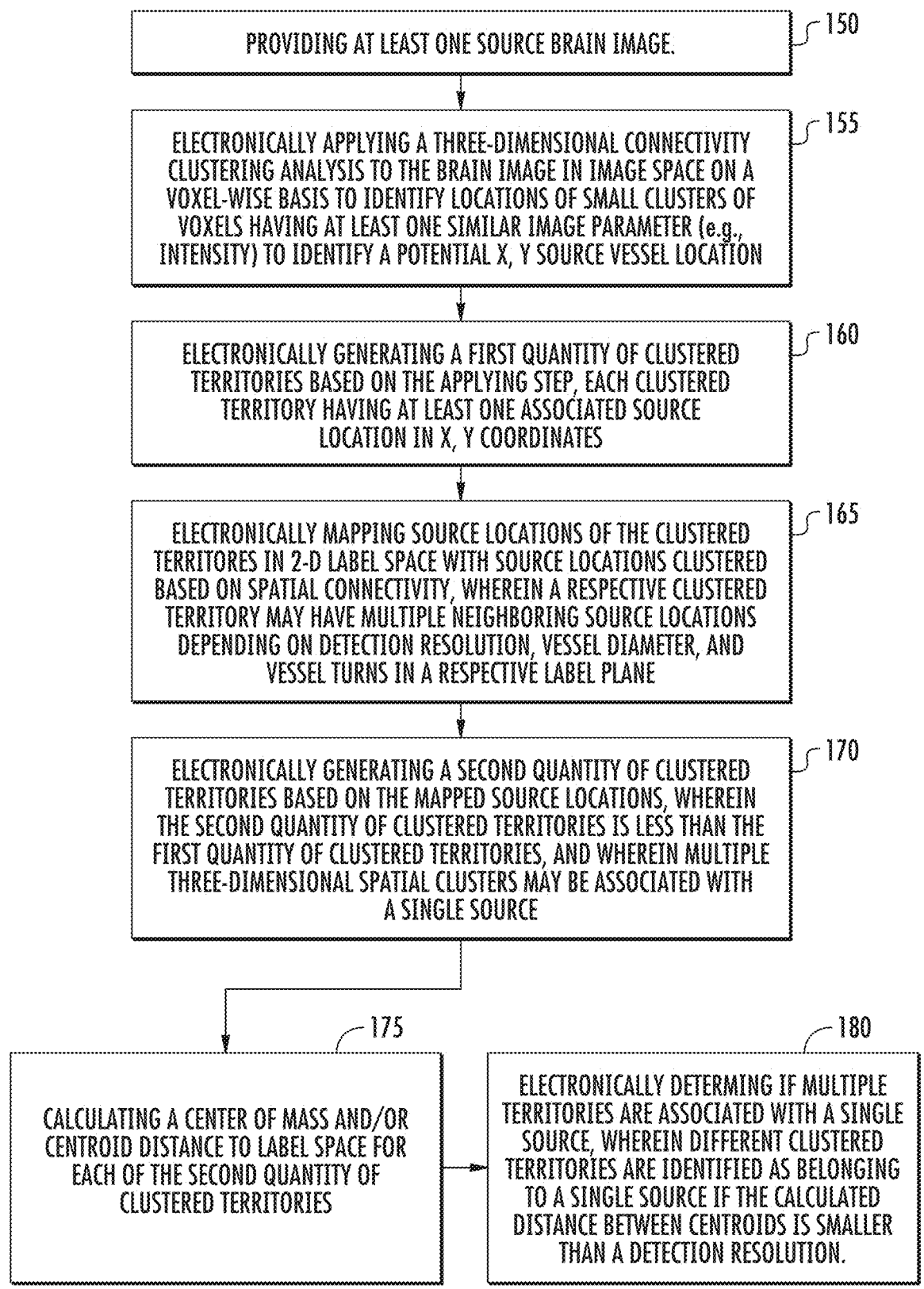
FIG. 3 is a flow chart of operations that can be used for vascular territory mapping according to embodiments of the present invention.

FIG. 3 is a flow chart of exemplary operations that can be used to carry out embodiments of the present invention. The operations can be implemented using a computer program product and/or at least one processor to provide an automated vascular segmentation algorithm based on vascular territory mapping. At least one source brain image can be provided from a medical image data set (block 150). A three-dimensional connectivity clustering analysis is electronically applied to the brain image data in image space on a voxel-wise basis to identify locations of small clusters of voxels having at least one similar image parameter (e.g., intensity) to identify a potential x, y source vessel location (block 155). A first quantity of clustered territories electronically generating based on the three-dimensional connectivity clustering analysis, each clustered territory having at least one associated source location in x, y coordinates (block 160). Then, source locations of the clustered territories in 2-D label space are electronically mapped with source locations clustered based on spatial connectivity (block 165). A respective clustered territory may have multiple neighboring source locations depending on detection resolution, vessel diameter, and vessel turns in a respective label plane. A second quantity of clustered territories can be electronically generated based on the mapped source locations (block 170). The second quantity of clustered territories can be less than the first quantity of clustered territories. Multiple three-dimensional spatial clusters may be associated with a single source. Then, a center of mass and/or centroid distance to label space is calculated for each of the second quantity of clustered territories (block 175). Then, a determination of whether multiple territories are associated with a single source is performed. Different clustered territories are identified as belonging to a single source if the calculated distance between centroids is smaller than a detection resolution (block 180).

Optionally, a color-coded weighted cerebral blood flow (CBF) territory map can be electronically generated, as may a source location estimation map with source locations in color and a numbered order associated with cluster size.

The MRI signal acquisition can be carried out without requiring the use of an administered contrast agent. The vascular color-coded tissue map can be used to identify functional changes in vascular distributions, as well as quantitative measures of blood flow per voxel. This information can be useful for individualized surgical planning and may be more predictive of a resultant stroke than velocity information from ultrasound or measures of ICA luminal diameter.

Embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (asics), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

Figure 4A:
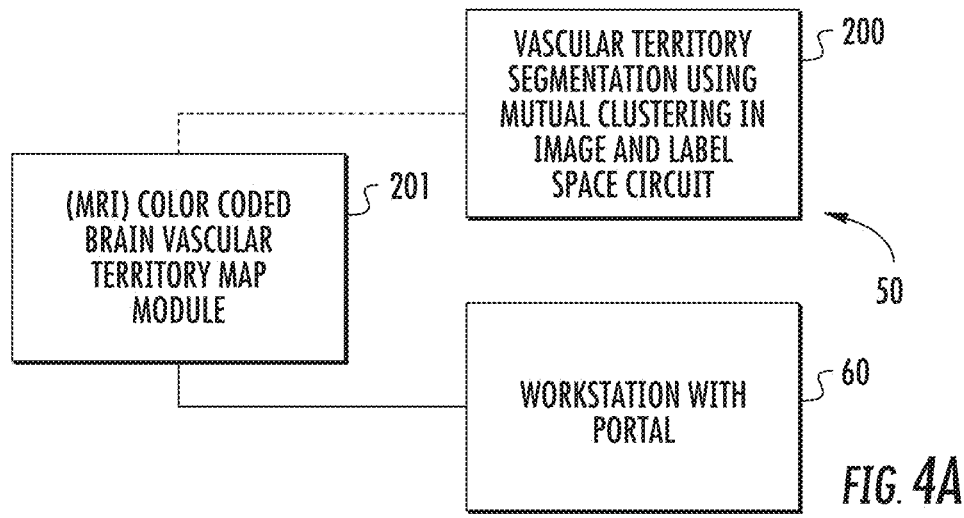
FIGS. 4A-4C are schematic illustrations of systems and circuits that can be configured to provide the Fourier encoded ASL according to embodiments of the present invention.
Figure 4B:
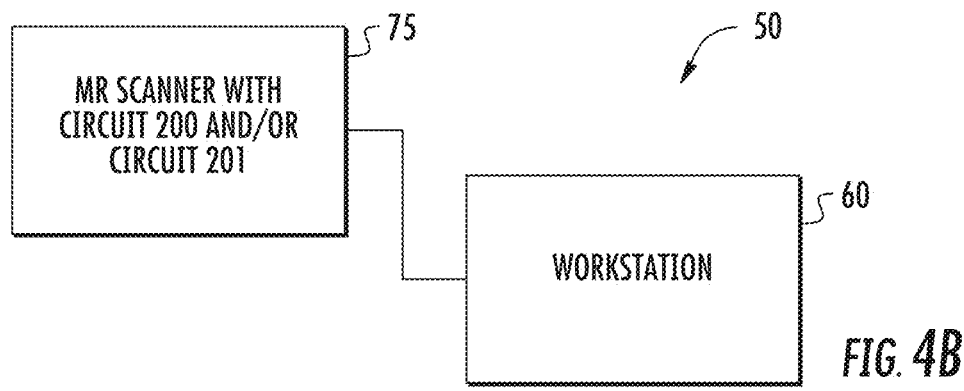
Figure 4C:
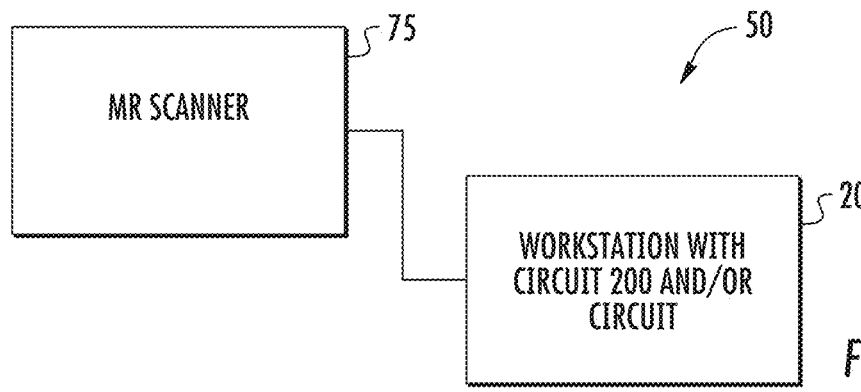

FIGS. 4A-4C illustrate exemplary image processing systems 10 with a Vascular Territory Segmentation circuit 200 and/or color coded brain vascular territory map module 201. The systems can be configured to automatically generate color vascular territory maps using rapid (e.g., under 5 minutes of active scanning) brain scans without requiring manual input for identification of arteries to carry out the image processing. The workstation and/or Scanner can each include at least one processor 60P, 75P, respectively, that can be configured to carry out all or part of the image analysis and image acquisition. The image analysis can be performed post-acquisition in a device separate from the Scanner used to acquire the image data.

FIG. 4A illustrates that the system 10 can include at least one workstation 60 that has an optional computer portal for accessing the module 201 and/or circuit 200. The module 201 can be held on a remote server accessible via a LAN, WAN, SAN or Internet. The workstation 60 can communicate with patient image data which may be held in a remote or local server, in the Scanner 75 or other electronically accessible database or repository. The workstation 60 can include a display with a GUI (graphic user input) and the access portal. The workstation can access the data sets via a relatively broadband high speed connection using, for example, a LAN or may be remote and/or may have lesser bandwidth and/or speed, and for example, may access the data sets via a WAN and/or the Internet. Firewalls may be provided as appropriate for security.

FIG. 4B illustrates that the circuit 200 and module 201 can be included in the MR Scanner 75 which can communicate with a workstation 60. The module 201 and/or circuit 200 can be integrated into the control cabinet of the MR Scanner with image processing or scan sequence control circuitry. FIG. 4C illustrates that the circuit 200 and/or module 201 can be integrated into one or more local or remote workstations 60 that communicates with the Scanner 75. Although not shown, parts of the circuit or module can be held on both the Scanner 75 and one or more workstations 60, which can be remote or local. The module and circuit can be combined or separated into further components.

The circuits and modules 200, 201 and methods of embodiments of the application can provide vascular territory mapping using non-contrast enhanced (NCE-) MRA methods.

Embodiments of the invention can be used clinically for various conditions including screening and analysis of impairments, disease and the like including, but not limited to, carotid artery stenosis. For the latter, it is expected that the degree of carotid stenosis can be identified based on a quantified collateral flow from the vascular territory mapping methods described herein.

The methods are also capable of resolving multiple sources feeding blood to a single voxel.

Figure 5:
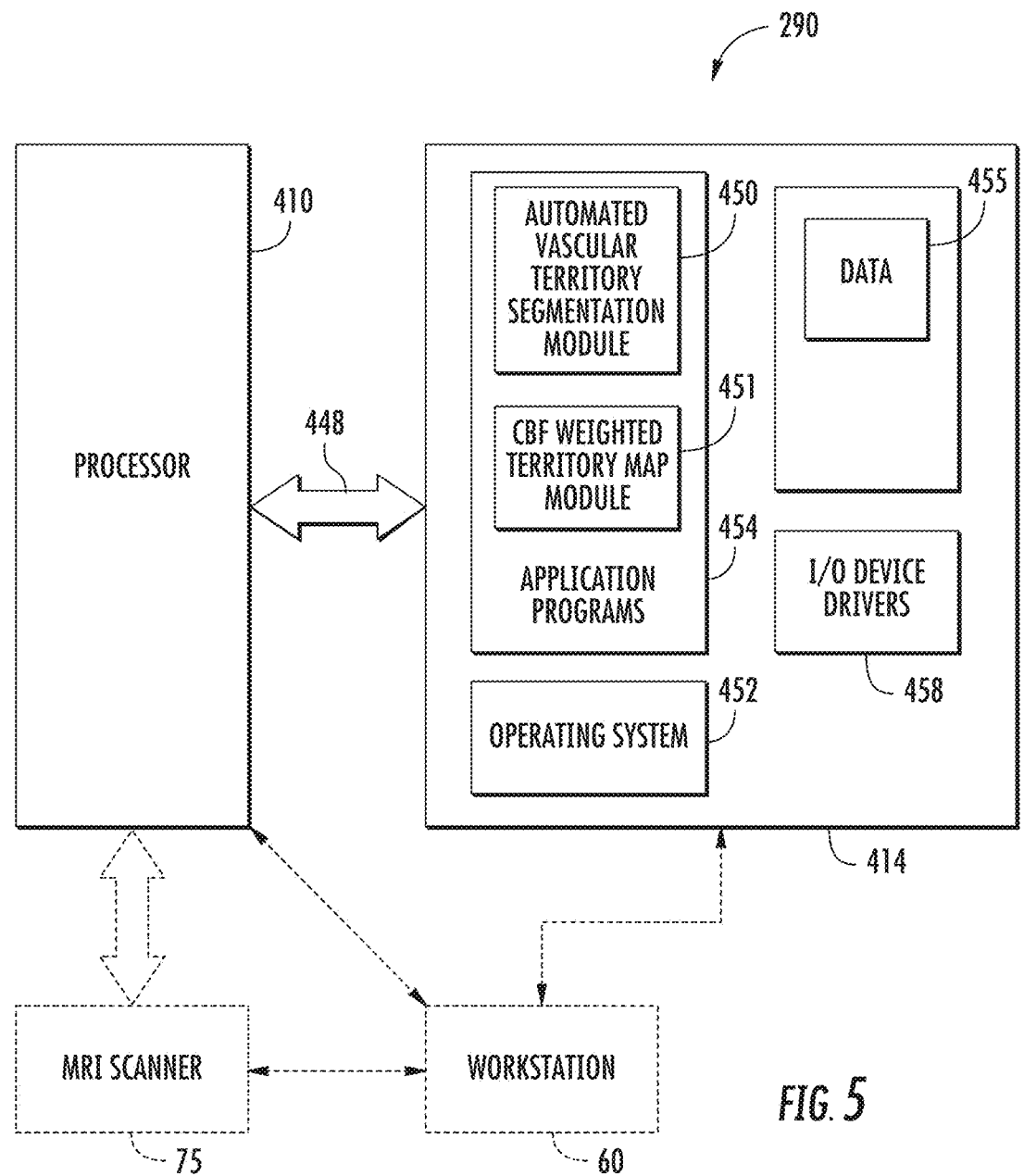
FIG. 5 is a block diagram of a data processing circuit according to embodiments of the present invention.

FIG. 5 is a schematic illustration of a circuit or data processing system 290. The system 290 can be used with any of the systems 10 and provide all or part of the circuit 200 and/or module 201. The circuits and/or data processing systems 290 data processing systems may be incorporated in a digital signal processor in any suitable device or devices. As shown in FIG. 5, the processor 410 can communicate with an MRI scanner 75 and/or workstation 60 with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 5 illustrates that the memory 414 may include several categories of software and data used in the data processing system: the operating system 452; the application programs 454; the input/output (I/O) device drivers 458; and data 455. The data 455 can include patient-specific MRI image (slice) data. FIG. 5 also illustrates the application programs 454 can include (an image reconstruction) Vascular segmentation Module 450 and a weighted CPF territory map Module 451 (with or without the color coded or color encoded source estimation map). Optionally, the application programs can also include a Fourier encoded ASL module that can cooperate with the Segmentation Module to generate color coded and/or encoded vascular maps of the brain. See, e.g., U.S. patent application Ser. No. 13/780,323, filed Feb. 28, 2013, entitled, Vessel Encoded Aterial Spin Labeling Using Fourier Encoding Suitable For Vascular Territory Mapping, the contents of which are hereby incorporated by reference as if recited in full herein.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, windowsxp or other Windows versions from Microsoft Corporation, Redmond, Wash., Unix or Linux or freebsd, Palm OS from Palm, Inc., Mac OS from Apple Computer, labview, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Module 450 being an application program in FIG. 5, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 5 which is intended to encompass any configuration capable of carrying out the operations described herein. Further, Module 450 can communicate with or be incorporated totally or partially in other components, such as an MRI scanner 75, interface/gateway or workstation 60.

The I/O data port can be used to transfer information between the data processing system, the workstation, the MRI scanner, the interface/gateway and another computer system or a network (e.g., the Internet) or to other devices or circuits controlled by the processor. These components may be conventional components such as those used in many conventional data processing systems, which may be configured in accordance with the present invention to operate as described herein.

Figure 6A:
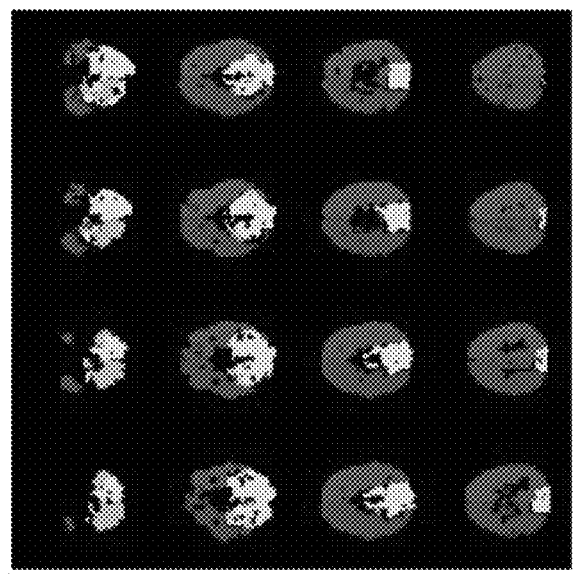
FIG. 6A are territory maps representing four major arteries according to embodiments of the present invention.
Figure 6B:
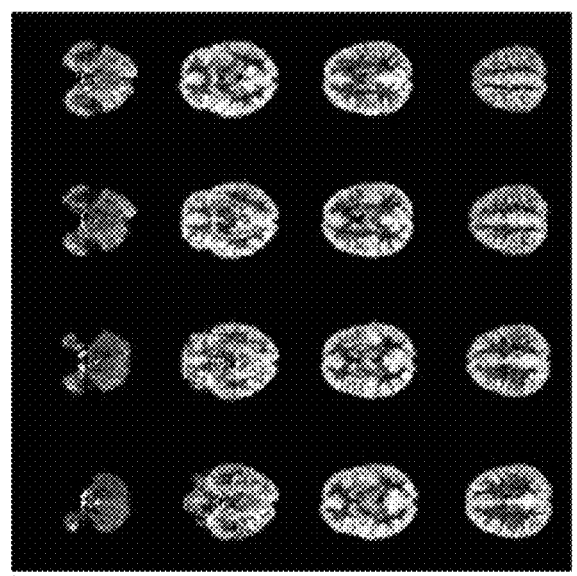
FIG. 6B shows corresponding CBF maps for FIG. 6A according to embodiments of the present invention.
Figure 6C:
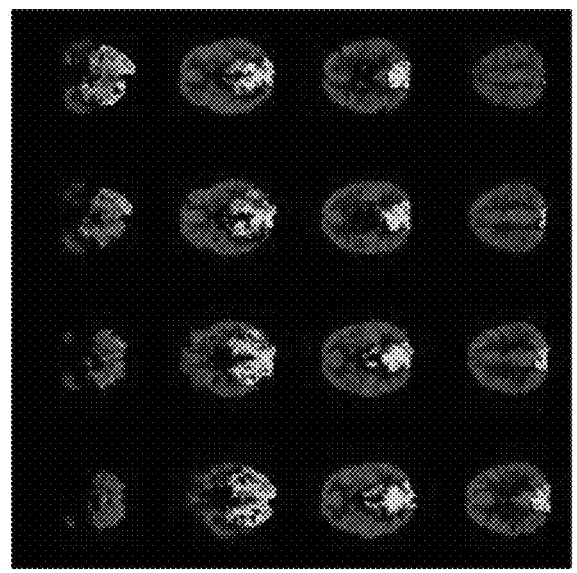
FIG. 6C are corresponding CBF weighted territory maps for FIG. 6A according to embodiments of the present invention.

FIGS. 6A-6C show an example of the invention when the tagging plane to be spatially encoded was located below the confluence to the basilar artery so as to encode internal carotid and vertebral arteries. FIG. 6A shows territory maps of internal carotid and vertebral arteries (blue: right internal carotid, red: left internal carotid, cyan: right vertebral, and yellow: left vertebral artery territories). FIG. 6B are corresponding CBF maps and FIG. 6C are CBF weighted territory maps indicating the source location and the amount of blood flow in a voxel.

The segmentation analysis contemplated by embodiments of the invention can be used with reconstruction of various medical image data sets whether "raw" or pre-processed using various processing methods such as, but not limited to that proposed by Wong et al, US 2012/0271157 A1, Mapping Vascular Perfusion Territories Using Magnetic Resonance Imaging, the content of which is hereby incorporated by reference as if recited in full herein. Stated differently, output from this other analysis can be used as input for the segmentation analysis tools/methods/programs/modules/algorithms described herein.

Embodiments of the invention provide a novel vascular territory mapping method requiring minimal operator intervention and simple post-processing routines that are suitable for clinical implementation. In addition, the methods can provide voxel-wise quantitative mapping of blood flow in the brain. The invention will be explained further by way of the non-limiting Examples below.

EXAMPLES

Probabilistic Cerebral Vascular Territory Atlases

Physiologically accurate mapping of cerebral blood flow in multiple separate vascular territories has a wide range of potential research and clinical applications, including the investigation and diagnosis of numerous common disease conditions that affect cerebral perfusion, such as migraine, carotid stenosis, and extracranialintracranial bypass before and after surgery. The identification of functional changes in vascular distributions, as well as quantitative measures of blood flow per voxel may be useful for individualized surgical planning, such as predicting the risk of potential iatrogenic ischemic stroke. Moreover, anatomical variations of the cerebral arteries and knowledge of this variation can avoid misdiagnosis. Probabilistic vascular territory atlases are well suited to take this vascular variation into account. Therefore, access to detailed vascular territory atlases may serve to advance understanding of the pathophysiology of diseases and the effects of interventions and treatments. To date, however, it is believed that only crude cerebral vascular territory atlases exist based on digitization of colorized figures, without any atlas generated by direct measurement of cerebral blood flow.

Methods

Data was obtained from 20 normal patients (4 male and 16 female, age range: 2-41 yrs.), with no evidence of disease or vascular abnormality. The data was collected on a 3 T Siemens SKYRA scanner with a 20 channel head/neck coil (Siemens AG, Erlangen, Germany). Vascular territory maps were obtained with a Fourier encoded ASL scan [Jung, 20th ISMRM: 581, 2012] using 2D EPI acquisition. Imaging parameters include 1.6 s tagging duration, 1.2s post-labeling delays, 22 ms/4 s TE/TR, 3.75 mm×3.75 mm in-plane resolution, 5 mm slice thickness, 24 axial slices. Fourier encoding parameters were: 9 cm×6.6 cm encoding FOV, 15×11 encoding steps (7×5 skipped steps), 6×6 mm encoding resolution, 56 repetitions, and 4 min scan time. The tagging plane to be spatially encoded was located below the confluence to the basilar artery so as to encode internal carotid and vertebral arteries. A high-resolution T1-weighted scan was also obtained for all subjects using a MP-RAGE sequence.

Source locations of the primary component from Fourier encoded ASL in x and y axis were processed using a territory segmentation algorithm [Jung et al., 21th ISMRM: 2154, 2013], which utilizes mutual connectivity information from both image and label spaces. The content of the Jung et al. references noted in the Examples section are hereby incorporated by reference as if recited in full herein.

The segments of four major arteries were categorized into two internal carotid and two vertebral arteries based on the relative position in the tagging plane. Each segment was confirmed by visual inspection of the location.

Figure 7A:
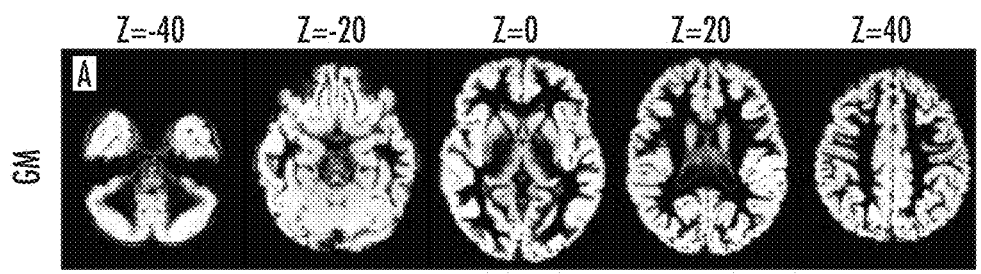
FIG. 7A are segmented and normalized gray matter maps at five locations.
Figure 7B:
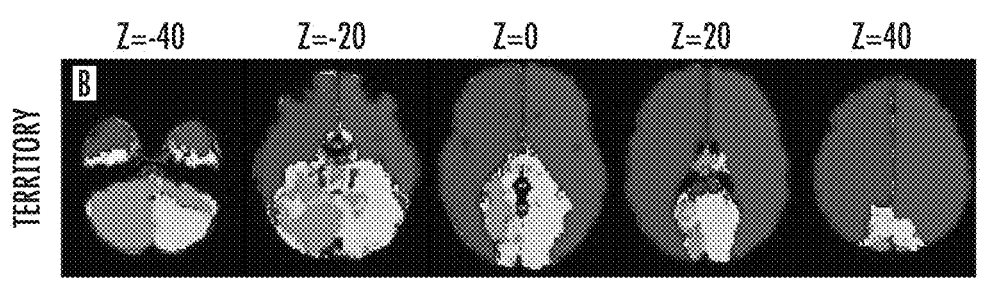
FIG. 7B are territory maps of internal carotid and vertebral arteries (blue: right internal carotid, red: left internal carotid, green: right vertebral, and yellow: left vertebral artery territories) according to embodiments of the present invention.
Figure 7C:
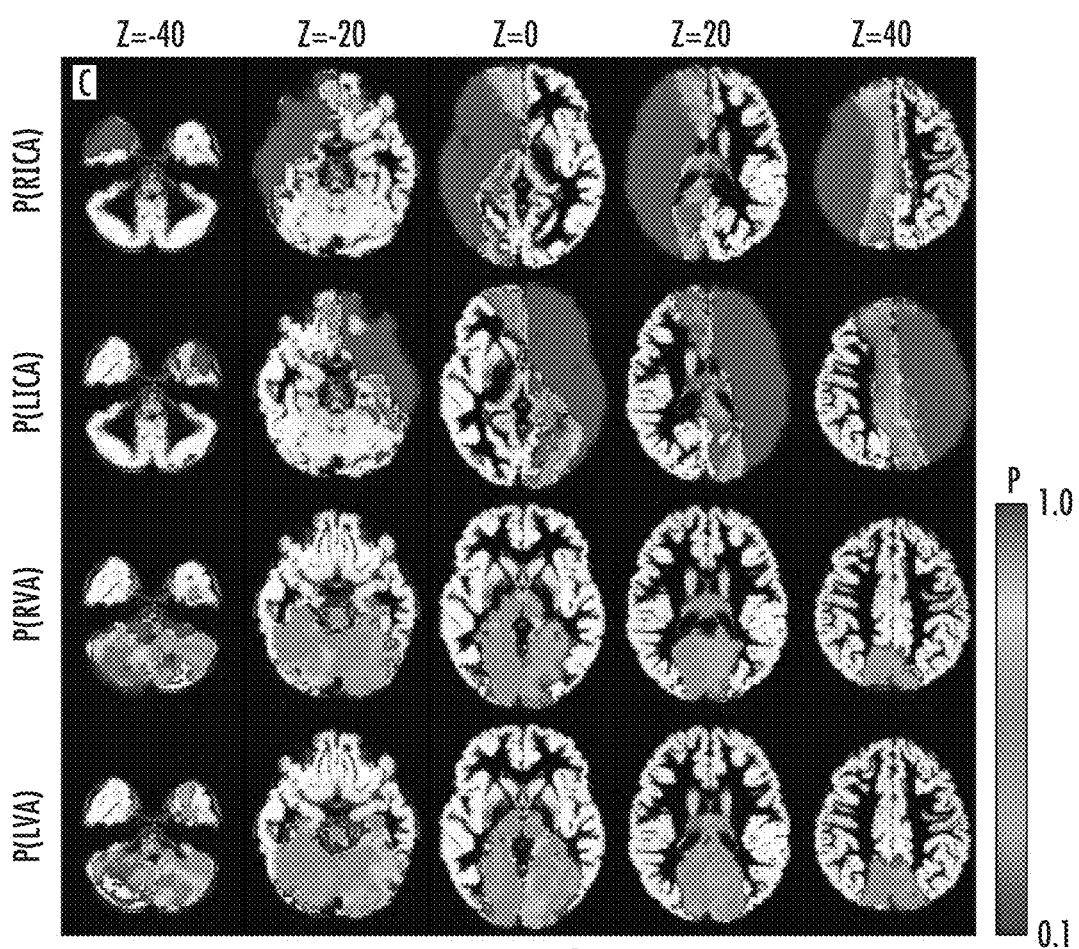
FIG. 7C are probabilistic territory maps of corresponding four major arteries according to embodiments of the present invention.

FIGS. 7A-7C illustrate images generated from the collected data. FIG. 7A are segmented and normalized gray matter maps at five locations. FIG. 7B are territory maps of internal carotid and vertebral arteries (blue: right internal carotid, red: left internal carotid, green: right vertebral, and yellow: left vertebral artery territories) according to embodiments of the present invention. FIG. 7C are probabilistic territory maps of corresponding four major arteries according to embodiments of the present invention.

T1-weighted images were processed for tissue segmentation and spatial brain normalization to the Montreal Neurological Institute (MNI) brain template using SPM8. The territory maps were coregistered to the structural T1 and normalized to MNI space using the transformation computed above. Per voxel basis probabilistic territory maps shown in FIG. 7C were computed by taking a ratio of the number of subjects having a certain source artery to the total number of subjects having any source artery. Vascular territory maps shown in FIG. 7B were generated by choosing the source artery having highest probability in a voxel.

Results

The vascular territory maps indicate that the internal carotid arteries supply blood to anterior and middle cerebral artery regions while the vertebral arteries primarily supply to posterior cerebral artery region. However, the probabilistic territory maps from individual feeding arteries represent the subject variability, which may not be shown with conventional vascular territory maps. Two interesting findings were observed: 1) 15% to 20% of subjects show blood supply to the right ACA region from contra-lateral flow of left ICA via the anterior communicating artery, but not vice versa, and 2) there is supply from the internal carotid arteries to the PCA region via the posterior communicating arteries, but no flow from PCA through posterior communicating arteries to supply ACA or MCA territories.

Discussions

These methods provide a frame-work for generating detailed vascular territory atlases that may have utility as clinical diagnostic and basic research tools. The acquisition of more data for normal subjects and those with diseases secondary to cerebral vascular; however, will be useful to determine the true utility as a clinical and research tool. With a larger sample size, gender-related and other group phenotypic variations may be explored. In addition, even though the cerebral vasculature is typically mature at birth, potential age-related variation may be of interest.

CONCLUSION

Thus, experiment-based vascular territory atlases of major arteries, which quantitatively map downstream cerebral perfusion may have important utility as a clinical diagnostic and basic research tool.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A non-invasive method of identifying blood flow information in a brain of a subject, comprising:
   obtaining at least one image data set of a brain of a subject;
   electronically generating per voxel basis probabilistic cerebral blood flow (CBF) territory maps of a plurality of major arteries in the brain of the subject representing quantitative blood flow in the brain from the obtained at least one image data set; and
   electronically displaying the generated probabilistic CBF territory maps in a color scale of probability of an identified source artery,
   wherein the generating the per voxel basis probabilistic CBF territory maps comprises taking a ratio of a number of subjects having a certain source artery to a number of subjects having any source artery whereby the per voxel basis probabilistic CBF territory maps represent the subject variability.

2. The method of claim 1, wherein each of the generated per voxel basis probabilistic CBF territory maps represent a defined color scale of high to low probability of an identified one of the arteries being the identified artery, and wherein the defined color scale of probability is displayed adjacent at least one of the probabilistic CBF territory maps.

3. The method of claim 1, wherein the color scale defines red as a highest probability, green as a lower probability and blue as a lowest probability.

4. The method of claim 1, wherein the displayed color-coded CBF probabilistic territory maps represent a right ICA, a left ICA, a right VA, and a left VA.

5. The method of claim 1, wherein the displayed probabilistic CBF maps are integrated with structural grey matter maps of T1-weighted MRI images of the subject.

6. A non-invasive method of identifying blood flow information in a brain of a subject, comprising:
   obtaining at least one image data set of a brain of a subject;

electronically generating per voxel basis probabilistic cerebral blood flow (CBF) territory maps of a plurality of major arteries in the brain of the subject representing quantitative blood flow in the brain from the obtained at least one image data set; and electronically displaying the generated probabilistic CBF territory maps in a color scale of probability of an identified source artery, wherein the generating the probabilistic CBF territory maps include directly measuring cerebral blood flow using source locations based on vascular connectivity in the at least one source image data set of the brain of the subject.

7. A non-invasive method of identifying blood flow information in a brain of a subject, comprising:

obtaining at least one image data set of a brain of a subject;

electronically generating per voxel basis probabilistic cerebral blood flow (CBF) territory maps of a plurality of major arteries in the brain of the subject representing quantitative blood flow in the brain from the obtained at least one image data set;

electronically displaying the generated probabilistic CBF territory maps in a color scale of probability of an identified source artery; and electronically generating color-coded CBF territory maps using the at least one data set, wherein the generated color-coded CBF territory maps are two-dimensional color-encoded blood flow maps that combines X and Y encoded primary and secondary peak data to visually indicate anterior/posterior and right/left directional components of respective feeding arteries using defined colors, the at least one CBF territory map further configured to visually indicate an amount of blood flow associated with each voxel using brightness of intensity, with increased brightness associated with increased blood flow.

8. A non-invasive method of identifying blood flow information in a brain of a subject, comprising:

obtaining at least one image data set of a brain of a subject;

electronically generating per voxel basis probabilistic cerebral blood flow (CBF) territory maps of a plurality of major arteries in the brain of the subject representing quantitative blood flow in the brain from the obtained at least one image data set;

electronically displaying the generated probabilistic CBF territory maps in a color scale of probability of an identified source artery, wherein the method further comprises, before the generating and displaying steps:

using vascular segmentation of the image data set to identify artery source locations using mutual connectivity in both image and label space;

analyzing three dimensional connectivity on a voxel-wise basis in an anterior/posterior direction and in a right/left direction; then identifying a first plurality of clustered territories, each territory having at least one source location in x, y coordinates; then mapping source locations clustered based on spatial connectivity, wherein a respective clustered territory can have multiple neighboring source locations; then generating a second plurality of clustered territories, less than the first plurality of clustered territories; and then calculating a centroid for each of the second plurality of clustered territories.

9. An image analysis circuit comprising:

at least one processor that is in communication with or at least partially onboard an MRI scanner, that is configured to:

obtain at least one image data set of a brain of a subject;

generate per voxel basis probabilistic cerebral blood flow (CBF) territory maps of a plurality of major arteries in the brain of the subject representing quantitative blood flow in the brain; and display the generated probabilistic CBF territory maps with source arteries provided in a color scale of probability, wherein the generated per voxel basis probabilistic CBF territory maps are generated by taking a ratio of a number of subjects having a certain source artery to a number of subjects having any source artery whereby the per voxel basis probabilistic CBF territory maps represent the subject variability.

10. The circuit of claim 9, wherein each of the generated per voxel basis probabilistic cerebral blood flow (CBF) territory maps represent an identified artery in a color scale of high to low probability as corresponding to that identified artery.

11. The circuit of claim 10, wherein the color scale defines red as a highest probability, green as a lower probability than red, and blue as a lowest probability.

12. The circuit of claim 9, wherein the displayed color-coded CBF probabilistic territory maps represent a right ICA, a left ICA, a right VA, and a left VA.

13. The circuit of claim 9, wherein the displayed probabilistic CBF maps are integrated with structural grey matter maps of T1-weighted MRI images of the subject.

14. An image analysis circuit comprising:

at least one processor that is in communication with or at least partially onboard an MRI scanner, that is configured to:

obtain at least one image data set of a brain of a subject;

generate per voxel basis probabilistic cerebral blood flow (CBF) territory maps of a plurality of major arteries in the brain of the subject representing quantitative blood flow in the brain; and display the generated probabilistic CBF territory maps with source arteries provided in a color scale of probability, wherein the at least one processor is further configured to directly measure cerebral blood flow using source locations based on vascular connectivity in the at least one source image data set of the brain of the subject.

15. An image analysis circuit comprising:

at least one processor that is in communication with or at least partially onboard an MRI scanner, that is configured to:

obtain at least one image data set of a brain of a subject;

generate per voxel basis probabilistic cerebral blood flow (CBF) territory maps of a plurality of major arteries in the brain of the subject representing quantitative blood flow in the brain; and display the generated probabilistic CBF territory maps with source arteries provided in a color scale of probability, wherein the at least one processor is further configured to generate color-coded CBF territory maps using the at least one image data set, wherein the generated color-coded CBF territory maps are two-dimensional color-encoded blood flow maps that combines X and Y encoded primary and secondary peak data to visually indicate anterior/posterior and right/left directional components of respective feeding arteries using defined colors, the at least one CBF territory map further configured to visually indicate an amount of blood flow associated with each voxel using brightness of intensity, with increased brightness associated with increased blood flow.

* * * * *